United States Patent [19]

Moss

[11] Patent Number: 5,601,571

[45] Date of Patent: Feb. 11, 1997

[54] SURGICAL FASTENER IMPLANTATION DEVICE

[76] Inventor: Gerald Moss, R.D. #1, West Sand Lake, N.Y. 12196

[21] Appl. No.: 445,642

[22] Filed: May 22, 1995

Related U.S. Application Data

[63] Continuation of Ser. No. 243,946, May 17, 1994, abandoned.

[51] Int. Cl.⁶ ........................................ A61B 17/04
[52] U.S. Cl. ........................ 606/139; 606/144; 606/187
[58] Field of Search ............... 606/139, 144–148, 606/187

[56] References Cited

U.S. PATENT DOCUMENTS

| | | |
|---|---|---|
| 3,103,666 | 9/1963 | Bone . |
| 3,675,639 | 7/1972 | Cimber . |
| 3,875,648 | 4/1975 | Bone . |
| 3,910,281 | 10/1975 | Kletschka et al. . |
| 3,961,632 | 6/1976 | Moossum . |
| 4,006,747 | 2/1977 | Kronenthal et al. . |
| 4,126,124 | 11/1978 | Miller . |
| 4,144,876 | 3/1979 | DeLeo . |
| 4,235,238 | 11/1980 | Ogiu et al. . |
| 4,669,473 | 6/1987 | Richards et al. . |
| 4,705,040 | 11/1987 | Mueller et al. . |
| 5,085,661 | 2/1992 | Moss . |

Primary Examiner—Gary Jackson
Attorney, Agent, or Firm— Schmeiser, Olsen & Watts

[57] ABSTRACT

A fastener implanting device used to implant a head portion of a "T" or "H"-shaped fastener within a body. The device has a needle portion and a grip portion. The needle portion encloses a longitudinally displaceable slide mechanism which is adapted to engage and eject the head portion of a fastener disposed within a slotted, distal end section of the needle. The longitudinal displacement of the slide mechanism is controlled by a mechanism located in the device's grip portion.

11 Claims, 3 Drawing Sheets

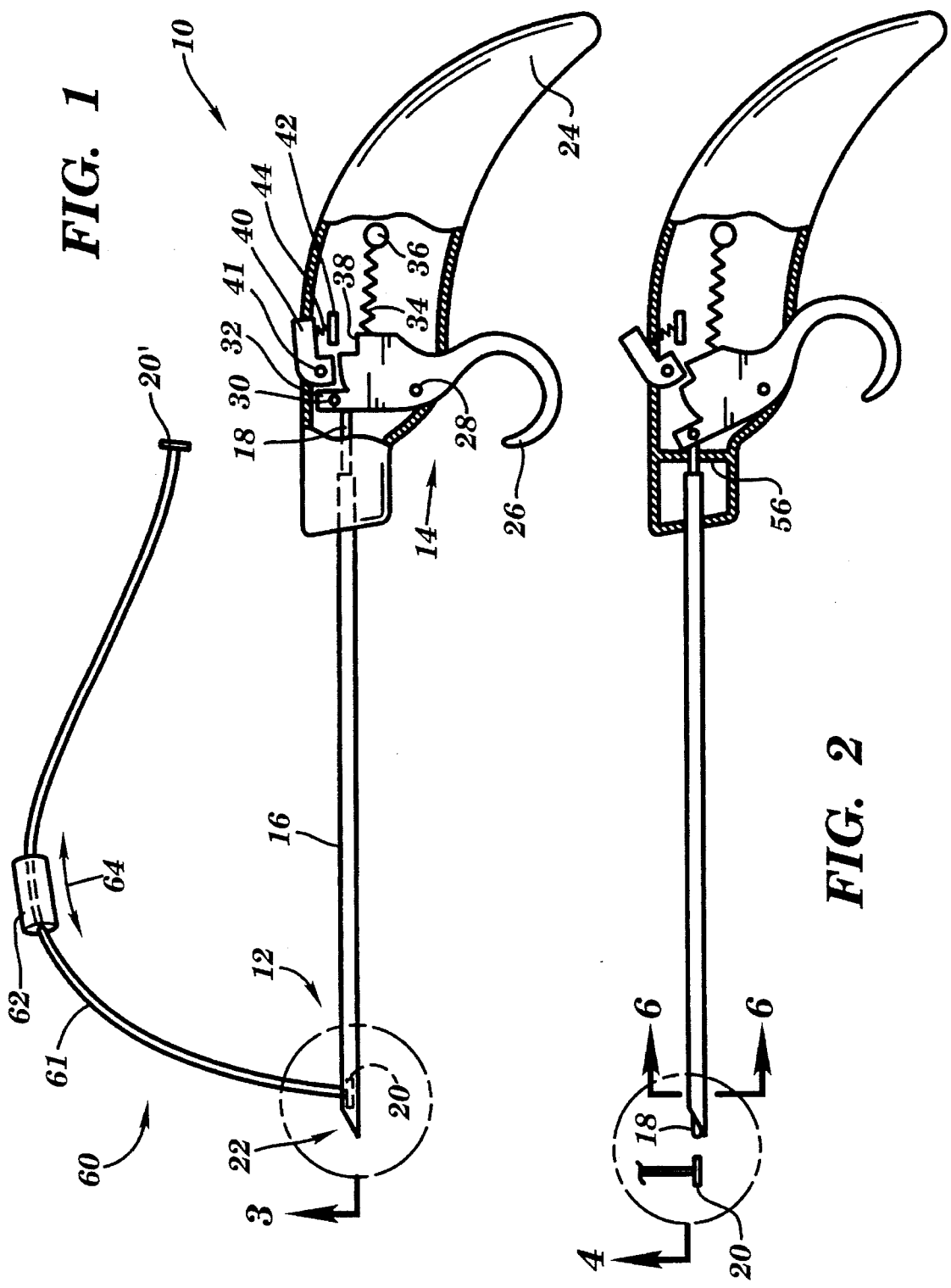

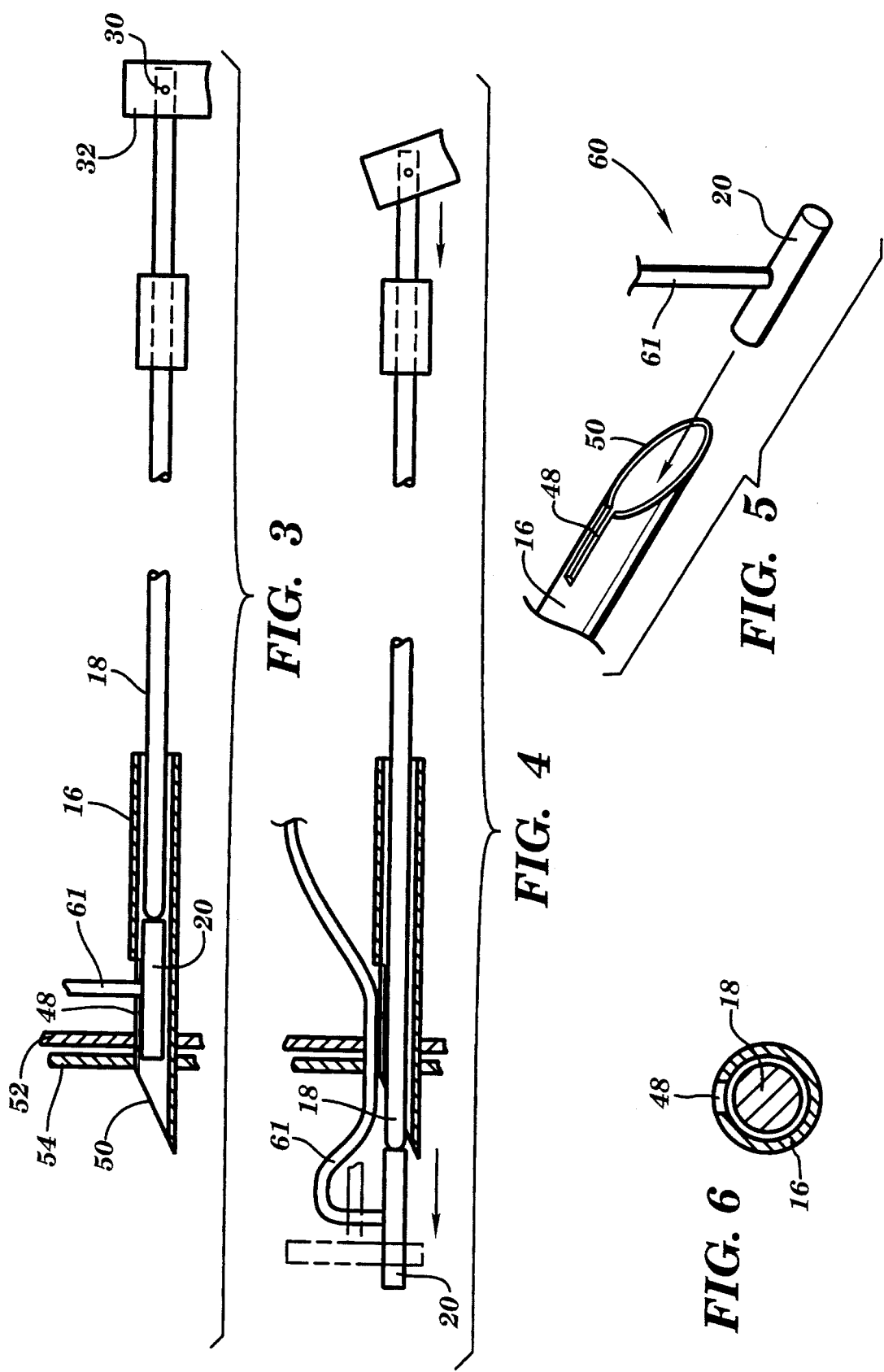

SURGICAL FASTENER IMPLANTATION DEVICE

This application is a continuation of application Ser. No. 08/243,946 filed May 17, 1994 now abandoned.

FIELD OF THE INVENTION

The present invention relates to surgical fastener devices and, more particularly, to a surgical fastener implantation device for implanting and releasing a surgical fastener within a body, wherein the surgical fastener is primarily utilized to secure a hollow organ to an outer tissue layer.

BACKGROUND OF THE INVENTION

As known in the art, surgical fastener devices have long been employed in a wide variety of medical procedures. Simple filament sutures (stitches), for example, are perhaps the most common type of anchoring device utilized to hold one segment of tissue to another. Recently, to avoid the time required to sew up a wound and tie the sutures, rapid fastening procedures have been developed, wherein an "H" or "T"-shaped fastener is inserted into the tissue about the wound in lieu of a sewn stitch to hold the tissue segments together.

In 1977, Kronenthal et al. received a patent (U.S. Pat. No. 4,006,747) on a surgical fastening method which involves the partial insertion of "H"-shaped fasteners through the tissue adjacent an incision using a hollow needle and a push-rod. Once in place, an end of the fastener is located on each side of the incision, with a connecting filament spanning the incision between the two ends of the fastener. The fastener maintains the tissue in place thereby facilitating the natural healing process.

The "H"-shaped fastener is also utilized in a number of non-medically related fastening systems. This type of fastener is commonly used in stores to affix price tickets to clothing. A number of devices have been employed to install the fasteners in clothing. Two patents, U.S. Pat. Nos. 3,103,666 and 3,910,281, have been issued to A. R. Bone for hand held devices that aid in the insertion of this type of fastener into clothing.

In recent years, a modification of the fastening system has become prevalent in surgical procedures. Ogiu et al. (U.S. Pat. No. 4,235,238), teaches a system wherein a needle for inserting a "T" shaped fastener is located within the end of an endoscope. Ogiu makes use of a hollow needle that has a longitudinally extending cavity sized to receive the head of the fastener. Once the needle has passed through the tissue on both sides of the wound, an obturator is pushed through the interior of the needle to dislodge the head of the fastener. The needle is then removed and an outer filament end of the fastener is tied to a lock member to maintain the closure of the wound.

Richards et al. (U.S. Pat. No. 4,669,474) illustrates a similar system that makes use of a "T" shaped fastener. Richards implants the head of the fastener into the tissue of a patient using a hollow needle and push-rod (obturator). The head of the fastener is shaped so that it strongly anchors itself to the tissue, therefore providing a secure fastening point within the body. The filament end of the fastener is then externally secured to the skin using a shaped retainer.

Mueller et al. (U.S. Pat. No. 4,705,040) teaches a system that uses a "T" shaped fastener to anchor a hollow organ to the skin. In Mueller, a hollow needle and obturator are again used to implant the head of the fastener. However, Mueller places the head of the fastener within the interior cavity of the organ to be anchored. Mueller then utilizes a movable lock member to secure the outer filament end of the fastener to the exterior of the skin.

The above prior art summaries are merely representative of portions of the inventions disclosed in each reference. In no instance should these summaries substitute for a thorough reading of each individual reference.

Presently available systems and methods for inserting and placing "T"-shaped or "H"-shaped fasteners suffer from a number of serious deficiencies. Firstly, as the inner obturator is pushed in a forward direction through the hollow outer needle to eject the fastener, the operator must push on the obturator along its longitudinal axis while simultaneously attempting to hold the needle stationary. Since the direction of this forwardly directed force is also along the longitudinal axis of the hollow outer needle, and the inner obturator is operationally coupled within the needle, it is extremely difficult to eject the fastener without displacing the outer hollow needle beyond its desired operational orientation. In a medical application, any unnecessary forward displacement of the outer hollow needle may produce unwanted, deleterious tissue damage, potentially increasing the duration of the healing process and/or increasing the risk of postoperative infection. Secondly, since it is generally easy to overcompensate for this forward force, an operator may accidentally pull the needle slightly outwards during the fastener ejection process, possibly resulting in the improper positioning of the fastener within the patient. Thirdly, the outer needle generally incorporates a stop mechanism for limiting the forward displacement of the enclosed obturator. If any difficulties occur during the insertion process, or if the fastener insertion system is inadvertently damaged before, during or after bodily insertion, the stop mechanism could, perhaps, be rendered inoperable or ineffective, thereby permitting the obturator to travel beyond the desired insertion location. As such, needless tissue damage may be inflicted by the unconstrained obturator. Unfortunately, such deficiencies combine to reduce the effectiveness and convenience of currently available "H"-shaped or "T"-shaped fasteners.

SUMMARY OF THE INVENTION

In order to avoid the disadvantages of the prior art, the present invention provides a surgical fastener implantation device for quickly and accurately inserting and releasing either a "T"-shaped or "H"-shaped surgical fastener into a body. The invention generally comprises an immovable, hollow outer needle having a beveled, slotted, distal end section for releasably receiving the head of a "T"-shaped or "H"-shaped surgical fastener, a longitudinally displaceable, inner slide mechanism, enclosed within the hollow outer needle, for engaging and ejecting the head portion of the fastener from the distal end section of the hollow outer needle after proper insertion within a patient, and a trigger shaped actuator, mounted within an ergonomically designed grip, for selectively displacing the inner slide mechanism within the hollow outer needle. A trigger locking mechanism is provided within the grip portion of the fastening device for releasably locking the inner slide mechanism in its forward, postejection position.

The present invention is ideally suited for use in securing organs in place. In operation, the operator loads the head of the fastener into the slot formed in the distal end section of the hollow outer needle. Preferably, the width of the slot is designed to be narrower than the diameter of the fastener head to prevent the premature dislodgement of the fastener head through the top of the slot. Prior to the insertion of the needle into the body tissue, the operator pulls the loose end of the fastener's filament portion toward the handle portion of the device. Next, the operator inserts the beveled end of the hollow outer needle into the body at a location where the tip of the needle will extend into an organ cavity. Upon proper positioning of the fastener head, the operator pulls the trigger shaped actuator, thereby displacing the slide mechanism toward the distal end of the needle, ultimately engaging and ejecting the fastener head within the organ cavity. To insure the complete ejection of the fastener head from the slotted distal end section of the hollow outer needle by preventing any unwanted reverse displacement of the slide mechanism, the trigger locking mechanism engages and locks the inner slide mechanism in its full ejection position, with the distal end of the slide mechanism disposed proximate the apex of the hollow needle bevel. The operator then removes the needle portion of the device from the body and "reloads" the needle with another fastener (or the opposing head of the same fastener—if "H"-shaped).

Advantageously, unlike the surgical fastener devices of the prior art, the instant invention does not require the application of a forwardly directed, longitudinal force during the ejection of the fastener head. Specifically, the trigger shaped actuator of the present invention must be pulled rearwardly to advance the inner slide mechanism in a forward direction within the hollow outer needle during the ejection process. As such, the surgical fastener implantation device substantially eliminates the ancillary tissue damage and inaccurate placement commonly associated with the operation of prior art fastening devices.

BRIEF DESCRIPTION OF THE DRAWINGS

These and other features of the present invention will become readily apparent upon reading the following detailed description and upon reference to the drawings in which:

FIG. 1 is a side elevational, partially cut-away view of a surgical fastener implantation device in accordance with the present invention, with the head portion of a fastener located within the slotted, distal end section of the hollow outer needle;

FIG. 2 illustrates the surgical fastener implantation device of FIG. 1 as the head portion of the fastener is ejected from the slotted, distal end section of the hollow outer needle by the longitudinally displaceable, inner slide mechanism;

FIG. 3 is an enlarged, cross-sectional view of the beveled, slotted, distal end section of the hollow outer needle, prior to the ejection of the fastener head within a hollow organ;

FIG. 4 is an enlarged, cross-sectional view of the beveled, slotted, distal end section of the hollow outer needle, after the ejection of the fastener head within a hollow organ;

FIG. 5 illustrates the loading of a fastener head within the slotted end section of the hollow outer needle;

FIG. 6 is a cross-sectional view of the surgical fastener implantation device, taken along line 6—6 of FIG. 1.

DETAILED DESCRIPTION OF THE DRAWINGS

Figure 7:
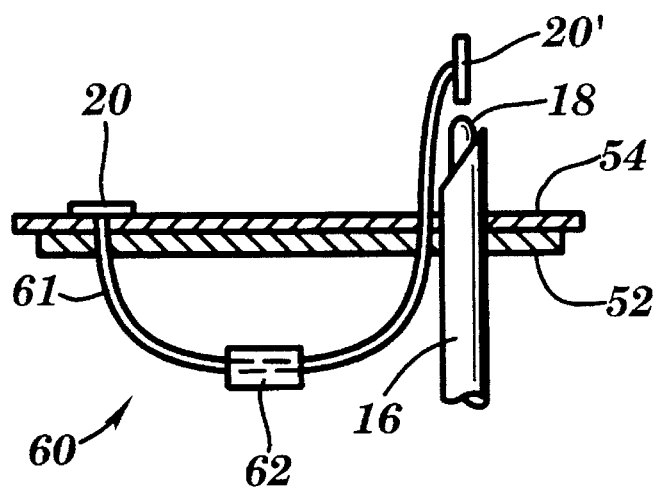
FIGS. 7 and 8 illustrate the implantation of the first and second heads of an "H"-shaped fastener within a hollow organ.
Figure 8:
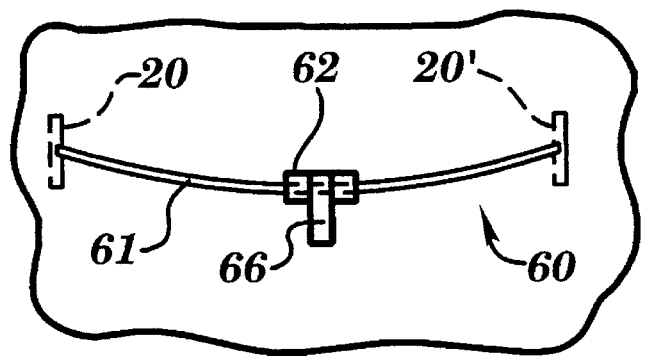

Referring now specifically to the drawings, there is illustrated a surgical fastener implanting device, generally designated as 10, in accordance with a preferred embodiment of the present invention, wherein like reference numerals refer to like components throughout the drawings.

The device 10 generally comprises an insertion portion 12 and a grip portion 14. The insertion portion 12 basically includes an immovable, hollow outer needle 16 and an elongated, substantially cylindrical, longitudinally displaceable, inner slide mechanism 18 for selectively engaging and ejecting the head 20 of a "T", "H" or other suitably shaped fastener disposed within the beveled, slotted, distal end section 22 of the hollow outer needle 16. The inner slide mechanism 18, when in its retracted position as detailed in FIG. 1, is fully enclosed within the hollow outer needle 16. As illustrated in FIG. 2, upon the rearwardly directed actuation of a manually actuated translation system (described hereinafter), the inner slide mechanism 18 is longitudinally displaced within the hollow outer needle 16, thereby ejecting the head 20 of a fastener from the beveled, slotted, distal end section 22 of the hollow outer needle 16. The needle is preferably of 18 gauge and has a length of approximately six inches.

The grip portion 14 has a rearwardly extending, ergonomically designed handle portion 24 that is sized to securely and comfortably fit within a user's clenched hand. Housed within the grip portion 24 is a manually actuated translation system that enables the user to selectively displace the inner slide mechanism 18 within the hollow outer needle 16.

The translation system includes a trigger shaped actuator 26 that is pivotally mounted within the grip portion 14 about a pivot pin 28. An end section of the longitudinally displaceable, inner slide mechanism 18 is similarly pivotally mounted about a pivot pin 30 to an upper, anterior portion 32 of the trigger shaped actuator 26. The hollow outer needle 16 is suitably anchored within the forward end of the grip portion 14 in a conventional manner, and is not further detailed.

A spring 34, which is affixed within the grip portion 14 at 36, is attached to a posterior portion of the trigger shaped actuator 26. The spring 34 is utilized to provide a clockwise biasing of the actuator 26. A top surface of the actuator 26 further includes a step 38 that is adapted to engage a lock member 40 in response to a rearwardly displacement of the actuator 26. The lock member 40 pivots about a pivot pin 41 and is coupled to an anchor 42 by a compression spring 44 which is adapted to provide a counterclockwise biasing of the lock member 40.

FIGS. 1, 3 and 5 illustrate the initial loading and positioning of a fastener head 20 within the beveled, slotted, distal end section 22 of the hollow outer needle 16. As most clearly shown in FIG. 5, the generally cylindrical head portion 20 (typically 1 cm in length) of an "H"-shaped fastening member 46 is placed within a slot 48 formed rearwardly of the beveled tip 50 of the needle, with the filament portion 51 of the fastener 46 extending upwardly through the slot 48. As detailed in cross-section in FIG. 6, the slot 48 is formed through the top of the hollow outer needle 16. Preferably, the beveled needle tip 50 has a 25 degree bevel, and the slot 48 extends approximately 7 mm from the heel of the bevel. Once the fastener head 20 has been appropriately positioned within the slot 48, the beveled needle tip 50 is inserted into the interior of an organ, such as the stomach, through the outer tissue layer 52 of the patient and the outer surface 54 of the organ.

Referring now specifically to FIGS. 2 and 4, there is illustrated the ejection of a fastener head 20 from the distal end section of the hollow outer needle 16. Specifically, as the trigger shaped actuator 26 is moved rearwardly from the position shown in FIG. 1, thereby pivoting the upper, anterior portion 32 of the actuator 26 in a forward direction about the pivot pin 28, the inner slide mechanism 18 is longitudinally displaced forwardly within the hollow outer needle, ultimately engaging and propelling the fastener head 20 from the end of the outer needle. When the trigger shaped actuator 26 reaches its rearwardmost position, the end of the inner slide mechanism extends to the apex of the beveled needle tip 50. Advantageously, the forward movement of the inner slide mechanism 18 is limited by the internal configuration of the grip portion 14. Specifically, as shown in FIG. 2, the grip portion 14 incorporates a front blocking wall 56 which is adapted to limit the forward rotation of the upper, anterior portion 32 of the actuator 26 about the pivot pin 28. As such, the end of the inner slide mechanism 18 is prevented from extending beyond the apex of the beveled needle tip 50, even if the actuator mechanism is defective or inadvertently damaged. As the trigger shaped actuator 26 reaches its rearwardmost position, the lock member 40 rotates in a counterclockwise direction due to the biasing of spring 44, ultimately engaging the step 38 which is formed proximate the top of the actuator 26. At this point, the inner slide mechanism 18 is locked in its postejection orientation.

The fastener ejection process may be accomplished by any of a number of different methods. The user can pull slightly on the filament portion 51 of the fastener as the inner slide mechanism 18 is displaced forwardly within the needle 16, thereby facilitating the ejection of the fastener head 20 from the slot 48. A second method of release is based on the material used for the fastener 46. Preferably, the fastener is made from a semi-resilient plastic such as nylon or polypropylene. The filament portion 51 is joined to the filament head 20 substantially perpendicular to the longitudinal axis of the fastener head. When the fastener is first inserted into the body, the filament 51 is pulled slightly so that it lies adjacent the body of the needle. As illustrated in FIG. 4, this causes a moment type of force on the end of the fastener due to the approximately ninety degree bending of the filament end adjacent the head portion of the fastener (i.e.—the filament is caused to lie substantially parallel to the longitudinal axis of the fastener head). When the inner slide mechanism 18 is displaced forwardly within the hollow outer needle 16, subsequently engaging the fastener head 20, the fastener head is propelled out of the slot 48 by the inherent resilience of the filament 51. The postejection orientation of the filament head 20, regardless of the ejection process, is illustrated in phantom in FIG. 4. Once the fastener head is ejected, the needle is withdrawn from the patient.

FIG. 7 shows a second end of an "H"-shaped fastener being inserted into a hollow organ. As shown, a first fastener head 20 has already been properly implanted. After loading the second fastener head 20' into the surgical fastener implantation device of the present invention, and subsequently inserting it into the body near the secured first head portion 20 of the fastener, the second fastener head 20' may be ejected and implanted as described above, thereby completing the attachment of the "H"-shaped fastener.

The foregoing description of the preferred embodiments of the invention has been presented for purposes of illustration and description. It is not intended to be exhaustive or to limit the invention to the precise form disclosed, and obviously many modifications and variations are possible in light of the above teaching. Such modifications and variations that may be apparent to a person skilled in the art are intended to be included within the scope of this invention as defined by the accompanying claims.

I claim:

1. A fastener insertion device for inserting a shaped fastener into a body, said shaped fastener including a head portion and a filament portion extending from said head portion, said fastener insertion device comprising:

an elongated, hollow needle member having a beveled, distal end portion, the beveled, distal end portion of said needle member including a slotted portion for releasably receiving the head portion of a shaped fastener therein;

a longitudinally displaceable slide mechanism movably enclosed within said elongated hollow needle member; and an actuator, operably coupled to said slide mechanism, for longitudinally displacing said slide mechanism within said elongated hollow needle member, said actuator including a trigger;

wherein, said actuator displaces said slide mechanism toward the distal end portion of said elongated, hollow needle member in response to a displacement of said trigger away from the distal end portion of said elongated, hollow needle member, and wherein the displacement of said slide mechanism toward the distal end portion of said elongated, hollow needle member ejects the head portion of a shaped fastener from the slotted portion of said needle member.

2. The fastener insertion device according to claim 1 wherein said elongated, hollow needle member has a longitudinal axis, and wherein the slotted portion of said needle member has a longitudinal axis which is substantially parallel to the longitudinal axis of said needle member.

3. The fastener insertion device according to claim 1 wherein said actuator further includes:

a releasable trigger lock for locking said trigger in a position wherein said slide mechanism is maintained in said second position.

4. The fastener insertion device according to claim 1 further including:

a housing attached to the elongated hollow needle member, with at least a portion of said actuator located within said housing.

5. The fastener insertion device according to claim 4 wherein said housing has an ergonomically shaped grip portion.

6. The fastener insertion device according to claim 4 wherein said housing includes a stop member for limiting the displacement of said trigger away from the distal end portion of said elongated, hollow needle member, thereby limiting the displacement of said slide mechanism toward the distal end portion of said elongated, hollow needle member.

7. The fastener insertion device according to claim 1 further including:

a biasing element, operatively connected to said longitudinally displaceable slide mechanism, for biasing said slide mechanism towards said first position.

8. A method for anchoring a hollow organ within a body comprising the steps of:

placing a head portion of a fastener within a slotted end portion of a hollow needle member;

inserting said hollow needle member within a hollow organ of a body to a point where the slotted end portion of said needle is within said hollow organ;

displacing a trigger away from the slotted end portion of said needle to displace a slide mechanism through said hollow needle member to engage and eject the head portion of said fastener from the slotted end portion of said hollow needle member;

removing the hollow needle member from the body; and pulling on a filament attached to said fastener head portion to thereby anchor said organ.

9. The method for anchoring a hollow organ within a body according to claim 8 further including the step of:

limiting the displacement of said trigger away from the slotted end portion of said needle, thereby limiting the displacement of said slide mechanism within said elongated, hollow needle member.

10. A method for placing a portion of a fastener within a body, said fastener including a head portion and a filament portion extending from said head portion, comprising the steps of:

placing the head portion of said fastener within a slotted end portion of a hollow insertion member;

inserting the slotted end portion of said hollow insertion member through a quantity of body tissue;

displacing a trigger away from the slotted end portion of said hollow insertion member to displace a slide mechanism through said hollow insertion member to engage and eject the head portion of said fastener from the slotted end portion of said hollow insertion member; and removing said hollow insertion member from the body tissue, with the filament portion of said fastener extending externally from said body tissue.

11. The method for placing a portion of a fastener within a body according to claim 10 further including the step of:

limiting the displacement of said trigger away from the slotted end portion of said hollow insertion member, thereby limiting the displacement of said slide mechanism within said hollow insertion member.

* * * * *